(12) United States Patent
Slack (10) Patent No.: US 9,402,543 B2
(45) Date of Patent: Aug. 2, 2016

(54) NTH LEADLESS ELECTRODE TELEMETRY DEVICE, SYSTEM AND METHOD OF USE

(71) Applicant: Darin Slack, Corona, CA (US)

(72) Inventor: Darin Slack, Corona, CA (US)

(*) Notice: Subject to any disclaimer, the term of this patent is extended or adjusted under 35 U.S.C. 154(b) by 0 days.

(21) Appl. No.: 14/722,496

(22) Filed: May 27, 2015

(65) Prior Publication Data

US 2016/0081550 A1 Mar. 24, 2016

Related U.S. Application Data

(63) Continuation-in-part of application No. 14/504,606, filed on Oct. 2, 2014, now Pat. No. 9,041,551.

(60) Provisional application No. 62/054,938, filed on Sep. 24, 2014.

(51) Int. Cl.
| | | |
|---|---|---|
| *A61B 5/00* | (2006.01) | |
| *H04Q 9/14* | (2006.01) | |
| *A61B 5/0408* | (2006.01) | |
| *A61N 1/39* | (2006.01) | |
| *H04Q 9/00* | (2006.01) | |

(52) U.S. Cl.
CPC .............. *A61B 5/0015* (2013.01); *A61B 5/0024* (2013.01); *A61B 5/0408* (2013.01); *A61N 1/39* (2013.01); *H04Q 9/00* (2013.01); *H04Q 9/14* (2013.01); *A61B 5/6833* (2013.01); *H04Q 2209/40* (2013.01)

(58) Field of Classification Search
None
See application file for complete search history.

(56) References Cited

U.S. PATENT DOCUMENTS

| | | |
|---|---|---|
| 6,289,238 B1 | 9/2001 | Besson et al. |
| 2013/0096641 A1 | 4/2013 | Strother et al. |

FOREIGN PATENT DOCUMENTS

CN 202146520 U 2/2012

*Primary Examiner* — Brian T Gedeon
(74) *Attorney, Agent, or Firm* — Lyman Moulton, Esq.

(57) ABSTRACT

A disclosed telemetry system comprises an Nth number of telemetry devices and an equal number of standard disposable circular electrode patches. A body of each telemetry device in the system includes a female snap receptor configured to attach to a single male snap post of an electrode patch. A wireless transmitter module is disposed in direct connection with each female snap receptor. Each wireless transmitter module transmits a signal to an electrical ground thereof to a receiver. A wireless receiver module is configured to receive and to process an Nth number of transmitted signals from the Nth number of telemetry devices into an Nth−1 number of signals where the number of signals is greater than zero. An interface on each telemetry device threads the devices in series to a single grounding device based on a connection and a disconnection of the single female snap receptor to the wireless transmitter module.

20 Claims, 11 Drawing Sheets

NTH LEADLESS ELECTRODE TELEMETRY DEVICE, SYSTEM AND METHOD OF USE

CROSS-REFERENCE TO RELATED APPLICATIONS

This application claims the benefit of the priority date of earlier filed U.S. Provisional Utility Application Ser. No. 62/054,938 filed Sep. 24, 2014 for Darin Slack, and U.S. Non-Provisional Utility application Ser. No. 14/504,606 filed Oct. 2, 2014 also for Darin Slack, each incorporated herein by reference in its entirety.

BACKGROUND AND FIELD OF INVENTION

In-patient health care for cardiac symptom diagnosis includes ECG and EKG analysis via electrode patches applied to a patient's skin near the heart. An Einthoven triangle is established by applying an electrode patch near the hip, preferably over non-musculature and another two electrode patches are applied to the chest. Multiple electrode patches help to establish where an ECG signal originates, which direction it is traveling and to establish a common 'ground.' Therefore it is common to apply 8, 12 and even 18 electrode patches to a patient who is non-ambulatory and wired to the diagnostic equipment. The multiple electrodes are commonly color coded in order to assist in establishing signal direction and ground.

Conventionally, the electrodes are connected by dedicated wires straight to the diagnostic equipment but getting from the patient even to a bedside piece of diagnostic equipment requires at least several feet of wires. However, leads can act as antennae for noise and produce artifacts of the desired signals. Lead artifacts distort a biological signal and must be filtered or ignored in the diagnostic process. Minimizing artifacts therefore becomes a priority in signal integrity and signal processing at the receiver. It is therefore desirable to minimize the lead wires to the multiple electrodes for cleaner signals and more accurate diagnostics.

Out-patient services cannot connect the electrode lead wires directly to the diagnostic equipment since it is not practical for a patient to carry the diagnostic equipment around with them. Therefore, a transceiver worn on the patient's wrist or carried in a pocket receives the multiple leads from the multiple electrode patches and communicates with the diagnostic equipment. However, this does not solve the lead artifact issues though it may shorten the lead wires from the electrode patches to the receiver carried with the patient.

Standard snap leads are a convenient and quick way of hooking a patient up to a diagnostic piece of equipment. However, it is also common for the electrode patches to come off the skin due to the leads pulling on them in outpatient everyday use and in-patient movements. This loss of contact results in loss of telemetry and exposes the patient to downtime and risks an unmonitored cardiac event in the interim time period(s). Also, when a patient takes a shower the lead wires are usually detached from the electrode patches because the receiver is not waterproof. This also exposes the patient to unattended telemetry downtime.

There is therefore a long felt need for a device and method to minimize lead wires from an electrode patch and allow a patient to take a shower and go about normal life as much as possible that has gone unmet until the present Applicants' disclosure.

SUMMARY OF THE INVENTION

A plurality of discrete electrode telemetry devices comprising a single female snap receptor configured in a body of a single electrode telemetry device is disclosed. The single female snap receptor is configured to attach to a single male snap post of a single standard disposable circular electrode patch. A wireless transmitter module is disposed immediately around and in direct connection with the single female snap receptor, the wireless transceiver configured to transmit a signal in reference to an electrical ground thereof to a remote receiver. An interface on each discrete electrode telemetry device is configured to thread the plurality of telemetry devices in series to a single grounding telemetry device based on a connection and a disconnection of the single female snap receptor to the wireless transmitter module and the electrical ground thereof. A switch activates and deactivates a transmission of the wireless transmitter module based on a respective snap connection and a disconnection between the single female snap receptor of the telemetry device and the single male snap post of the electrode patch.

A telemetry system comprising an Nth plurality of wireless and discrete electrode leadless telemetry devices and an equal plurality of standard disposable electrode patches is also disclosed. The system includes a single female snap receptor configured in a leadless body of each of the discrete electrode telemetry devices. Each female snap receptor is configured to attach to a single male snap post of an electrode patch. The system also includes a wireless transmitter module disposed immediately around and in direct connection with each female snap receptor. Each respective wireless transmitter module is configured to transmit a signal in reference to an electrical ground thereof to a receiver. The system additionally includes an interface on each discrete electrode telemetry device configured to thread the plurality of telemetry devices in series to a single grounding telemetry device based on a connection and a disconnection of the single female snap receptor to the wireless transmitter module and the ground thereof. The system further includes a wireless receiver module configured to receive and to process an Nth number of transmitted signals from the Nth number of telemetry devices into an Nth−1 number of signals where the number of signals is greater than zero. There is Nth−1 number of signals because at least one of the Nth telemetry devices is configured as a ground or zero volt reference for the rest of the Nth number of telemetry devices.

The telemetry system receiver module may reside in one of a cell phone casing and the cell phone itself. The cell phone casing is configured to communicate a composite transmission to the cell phone for processing or a stand-alone processor unit capable of communicating with a personal computer.

A method for telemetry including an Nth number of button-like wireless and leadless telemetry devices and an equal number of standard disposable electrode patches attachable to a patient is further disclosed. The method includes providing a single female snap receptor configured in a body of each of the discrete electrode telemetry devices, each female snap receptor configured to attach to a single male snap post of the plurality of electrode patches. The method also includes transmitting a signal in respect to an electrical ground thereof from the respective female snap receptor to a remote receiver via a wireless transmitter processor disposed immediately around and in direct connection with each female snap receptor. The method yet includes threading the plurality of telemetry devices in series to a single grounding telemetry device based on a connection and a disconnection of the single female snap receptor to the wireless transmitter module and the ground thereof. The method additionally includes receiving and processing an Nth number of the transmitting signals from the Nth number of telemetry devices into an Nth−1 number of signals greater than zero via a receiver processor.

The method further includes creating an Nth-1 number of composite signals including an Nth transmitting signal and a common ground reference signal. The method yet includes threading the plurality of telemetry devices in series to a single grounding telemetry device via an interface on each telemetry device based on a connection and a disconnection of the single female snap receptor to the wireless transmitter module and the ground thereof.

Other aspects and advantages of embodiments of the disclosure will become apparent from the following detailed description, taken in conjunction with the accompanying drawings, illustrated by way of example of the principles of the disclosure.

Throughout the description, similar reference numbers may be used to identify similar elements depicted in multiple embodiments. Although specific embodiments of the invention have been described and illustrated, the invention is not to be limited to the specific forms or arrangements of parts so described and illustrated. The scope of the invention is to be defined by the claims appended hereto and their equivalents.

DETAILED DESCRIPTION

Reference will now be made to exemplary embodiments illustrated in the drawings and specific language will be used herein to describe the same. It will nevertheless be understood that no limitation of the scope of the disclosure is thereby intended. Alterations and further modifications of the inventive features illustrated herein and additional applications of the principles of the inventions as illustrated herein, which would occur to one skilled in the relevant art and having possession of this disclosure, are to be considered within the scope of the invention.

Figure 1:
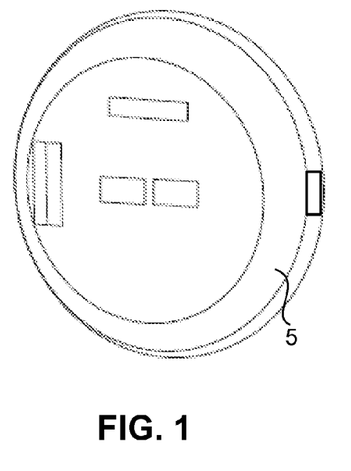
FIG. 1 is a top perspective view of an Nth leadless telemetry device in accordance with an embodiment of the present disclosure.

Throughout the present disclosure, the term 'sensor' refers to disclosed components that may include an electrode patch, an amplifier, a transmitter and any other components associated with the disclosed telemetry device in transmitting, detecting, converting and relaying signals from the human body to electric and electronic systems and devices. Also, as used in the present disclosure, the term 'single' refers to a solitary electrode patch and telemetry unit as opposed to prior art including multiple patches and or multiple electrodes or multiple telemetry devices. Additionally, the term 'multiplexer' refers to a device that selects one of several analog or digital input signals and forwards the selected input into a single line. A multiplexer of 2 inputs has n select lines, which are used to select which input line to send to the output. The term 'electrode patch' as used in the present disclosure includes an electrical conductor used to make contact with a nonmetallic part of a circuit where a patient is the start of a circuit in accordance with an embodiment of the present disclosure. The patch component is a standard disposable patch with sticky adhesive applied to an underside as is standard in the art of electrode patches. The telemetry device disclosed therefore is not an electrode nor an electrode patch but a novel and unobvious device for the quick and convenient gathering of telemetry information from an ambulatory patient via wireless transmissions over radio waves or ultrasonic waves and any other types of communicable waveforms. The term 'electrical ground' refers to a voltage reference over which a signal level is taken or measured and that provides a return for current in FIG. 1 is a top perspective view of an Nth leadless telemetry device in accordance with an embodiment of the present disclosure. A telemetry device 5 comprising a female snap receptor 10 (not depicted) configured in a body of the telemetry device 5 is disclosed. The female snap receptor 10 is configured to attach to a male snap post 15 (not depicted) of a standard disposable electrode patch 20 (not depicted). A wireless transmitter module 25 internal to the telemetry device 5 is disposed immediately around and in direct connection with the female snap receptor 10, the wireless transmitter configured to transmit a signal in reference to an electrical ground thereof from the female snap receptor 10 to a remote receiver 30. A programmable switch 35 also internal to the telemetry device 5 activates and deactivates a transmission of the wireless transmitter module 25 based on a respective snap connection and a disconnection between the female snap receptor 10 of the telemetry device 5 and the male snap post 15 of the electrode patch 20. The switch 35 may be implemented in hardware or in software where a non-transitory computer readable medium has computer useable program code executable to perform operations of a physical or an electronic switch configured to control the transmission of the wireless transmitter module despite a snap connection between the female snap receptor and the male snap post. This override function of the programmable switch is configured to override the activation switch 35 and control the transmission of the wireless transmitter module 5 regardless of the snap connection between the female snap receptor 10 and the male snap post 15. This function gives flexibility to power saving options for the telemetry device as a master, a slave and an inactive device.

Figure 2:
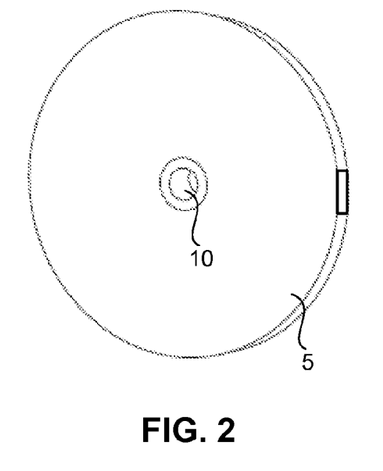
FIG. 2 is a bottom perspective view of an Nth leadless telemetry device illustrating the female snap receptor at the center of the device in accordance with an embodiment of the present disclosure.

FIG. 2 is a bottom view of a telemetry device illustrating the exposed bottom of the electrode at the center of the patch in accordance with an embodiment of the present disclosure. The telemetry device 5 is depicted as a disc-like shape to be compatible with a disc-like electrode patch 20. The female snap receptor 10 may include pinching springs configured to clasp the male snap post 15 and any other means common in the art of snap connectors. The male snap post may also be configured in a bulbous head to enable a pinching around the post thereof. The pinching springs and the female snap receptor 10 may comprise metal and conductive materials for transferring the biological signal coming from the patient via an electrode patch to the wireless transmitter module 25. The female snap receptor 10 is configured to completely enclose the male snap post 15 so that the telemetry device 5 may sit flush onto the electrode patch 20.

Figure 3:
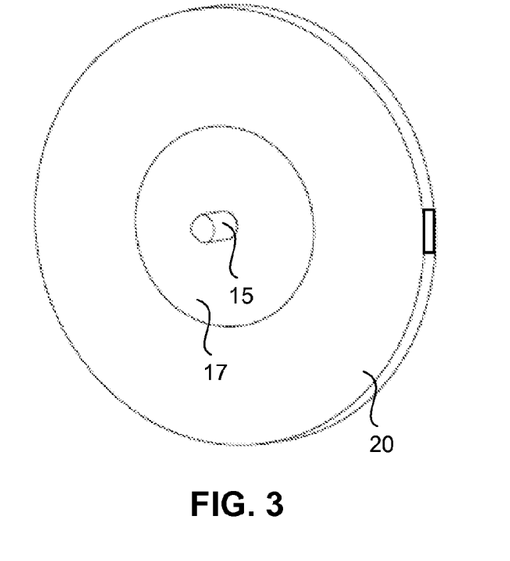
FIG. 3 is a top perspective view of a standard disposable medical grade electrode and male snap post in accordance with an embodiment of the present disclosure.

FIG. 3 is a top perspective view of a standard disposable medical grade electrode and male snap post in accordance with an embodiment of the present disclosure. The electrode patch 20 includes a male snap post 15 and a nipple area 17 comprising a conductive area beneath and around the male snap post 15. A conductive gel may be included below the male snap post 15 for making contact with a patient's skin. The electrode patch 20 is a standard disposable medical grade patch. The male snap post may also be configured with a bulbous head and a narrower post to enable the female snap receptor to clasp around the post and secure the bulbous head.

Figure 4:
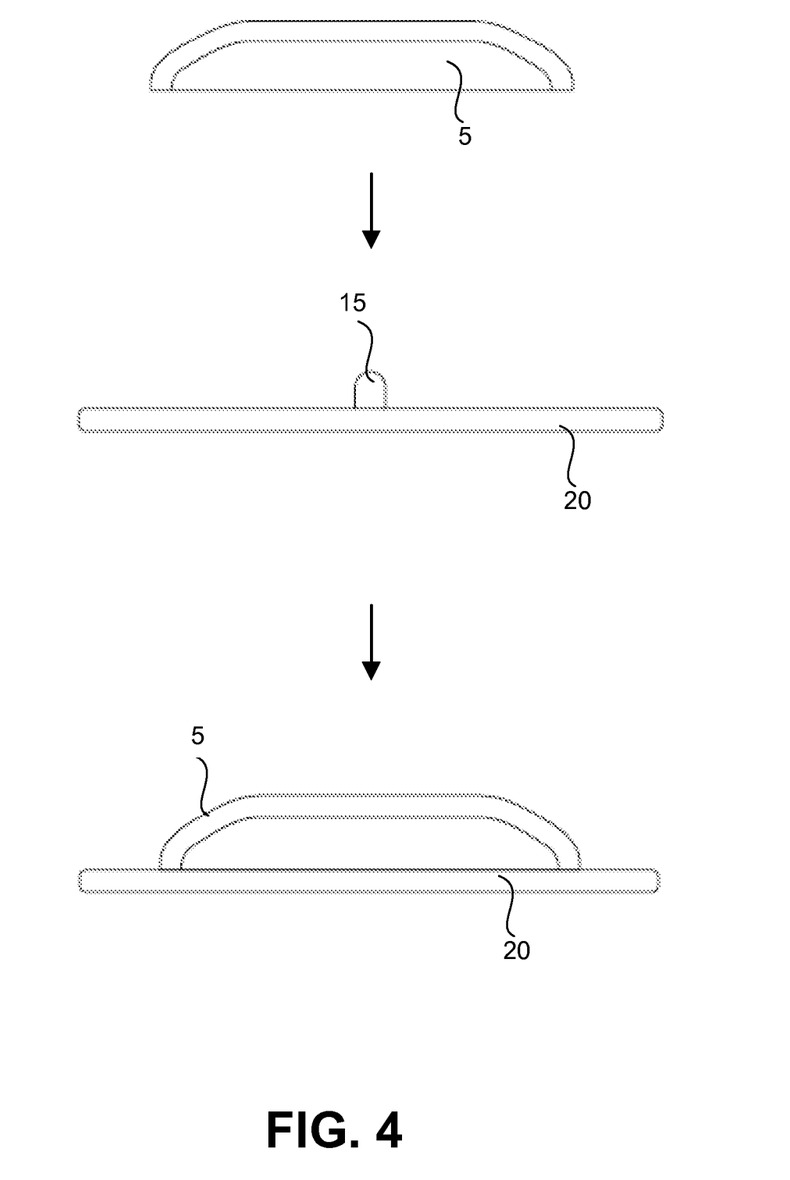
FIG. 4 is a side view of a telemetry device, a standard disposable medical grade electrode and a snapped combination pair in accordance with an embodiment of the present disclosure.

FIG. 4 is an exploded side view of a telemetry device, a standard disposable medical grade electrode and a snapped combination pair in accordance with an embodiment of the present disclosure. Same or similar characteristics depicted in other figures may share the same reference numbers depicted herein. The body of the telemetry device 5 is configured in a saucer-like chamfered perimeter shape having a radius similar to a radius of a US minted quarter and a total weight less than a weight of a US minted quarter. This low profile chamfered shape of the telemetry device 5 allows a patient to 'wear' it without snagging undergarments and go about their normal daily activities unencumbered by the telemetry process in progress. The disclosed telemetry device may even resemble a large button.

The wireless transmitter module 25 may be an ultrasound or a radio frequency transmitter such as Bluetooth® configured to transmit a signal in reference to an electrical ground thereof via ultrasound or radio waves from the female snap receptor 10 to a remote receiver 30 configured to receive an ultrasound or a radio transmission. Benefits of an ultrasound personal area network include lower cost and lower interference from other ultrasound sources. However, ultrasound personal area networks have reflection and obstacles issues not present in radio frequency transmissions. Therefore, a hybrid ultrasound and radio frequency transmission may be included in an embodiment of the present disclosure.

Figure 5:
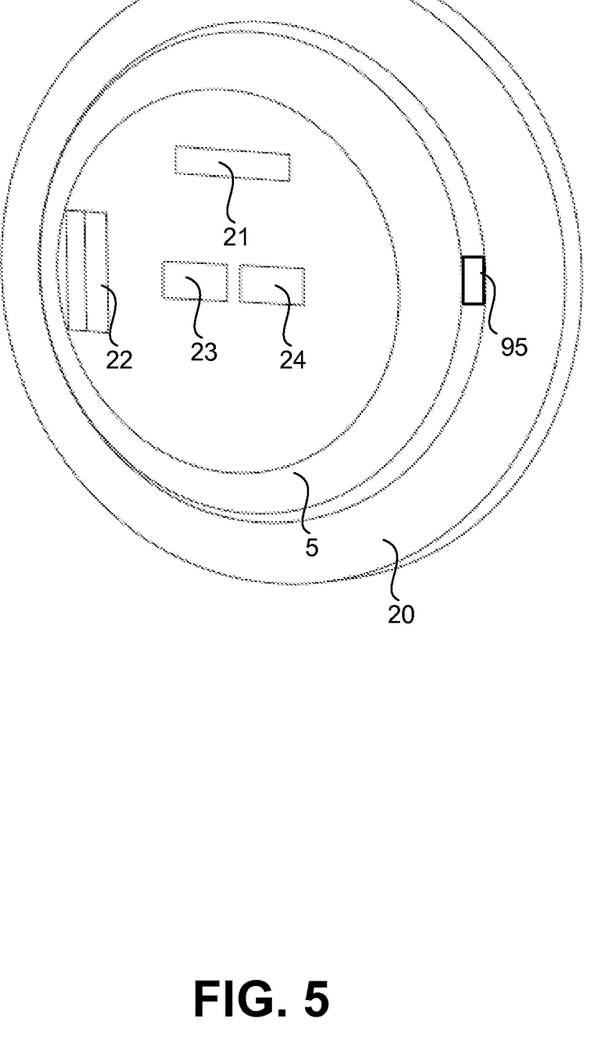
FIG. 5 is a perspective close-up view of the Nth leadless telemetry device illustrating status indicators and identifiers, etc in accordance with an embodiment of the disclosure.

FIG. 5 is a perspective close-up view of an Nth leadless telemetry device illustrating status indicators and identifiers, etc. in accordance with an embodiment of the present disclosure. Same or similar characteristics depicted in other figures may share the same reference numbers depicted herein. The vent 21 may be used for input output to the telemetry device such as a speaker vent or a sonic receiver. The LED windows 22 may identify the telemetry device from the Nth number used in any system by color coding the device based on where it is placed on a patient. Push buttons 23 and 24 may be used to activate and deactivate the telemetry device or to perform other functions according to model type and lot release date. Status indicator and identification windows, etc. are only representative of an embodiment and are not intended to restrict other features and characteristics are disclosed herein. An interface 95 on each discrete electrode telemetry device may be configured to thread the plurality of devices in series to a single grounding device based on a connection and a disconnection of the single female snap receptor to the wireless transmitter module and the electrical ground thereof.

An Nth number multicolor light emitting diode (LED) 50 may also be implemented as various color LEDs in an embodiment of the telemetry device wherein an Nth color LED corresponds to a predeterminable Nth telemetry device number for signal identification purposes. The number N may range from 1 to 8, to 12, to 18 and any practical number of telemetry devices to be applied to a patient. The Nth telemetry device number is configured to be transmitted with the transmitted signal so the LED color may 'color code' a specific electrode patch placement as done in the prior art with colored leads.

In an embodiment of the disclosure, the wireless transmitter module 25 is configured to act as one of a master and a slave in one network and to alternatively act as a slave in another network in a multiple network master-slave protocol. This master-slave multiple network embodiment enables communication by more than eight telemetry devices and at least one receiver in a Bluetooth® implementation where a single network is limited to one master and seven slaves.

In a Bluetooth® piconet, one master can communicate up to 7 active slaves, there can be some other up to 248 devices which are in sleep mode (may participate to communication actively when another active device goes into sleep mode). In Bluetooth® scatternets (interconnected piconets) number of devices are not limited. Some slaves used as a bridge by participating two or more piconets.

A piconet is the type of connection that is formed between two or more Bluetooth-enabled devices such as modern cell phones or PDAs. Bluetooth® enabled devices are "peer units" in that they are able to act as either master or slave. However, when a piconet is formed between two or more devices, one device takes the role of 'master', and all other devices assume a 'slave' role for synchronization reasons. Piconets have a 3-bit address space, which limits the maximum size of a piconet to 8 devices ($2^3$=8), i.e. 1 master and 7 slaves.

A scatternet is a number of interconnected piconets that supports communication between more than 8 devices. Scatternets can be formed when a member of one piconet (either the master or one of the slaves) elects to participate as a slave in a second, separate piconet. The device participating in both piconets can relay data between members of both ad hoc networks. However, the basic Bluetooth® protocol does not support this relaying—the host software of each device would need to manage it. Using this approach, it is possible to join together numerous piconets into a large scatternet, and to expand the physical size of the network beyond Bluetooth's limited range.

Figure 6:
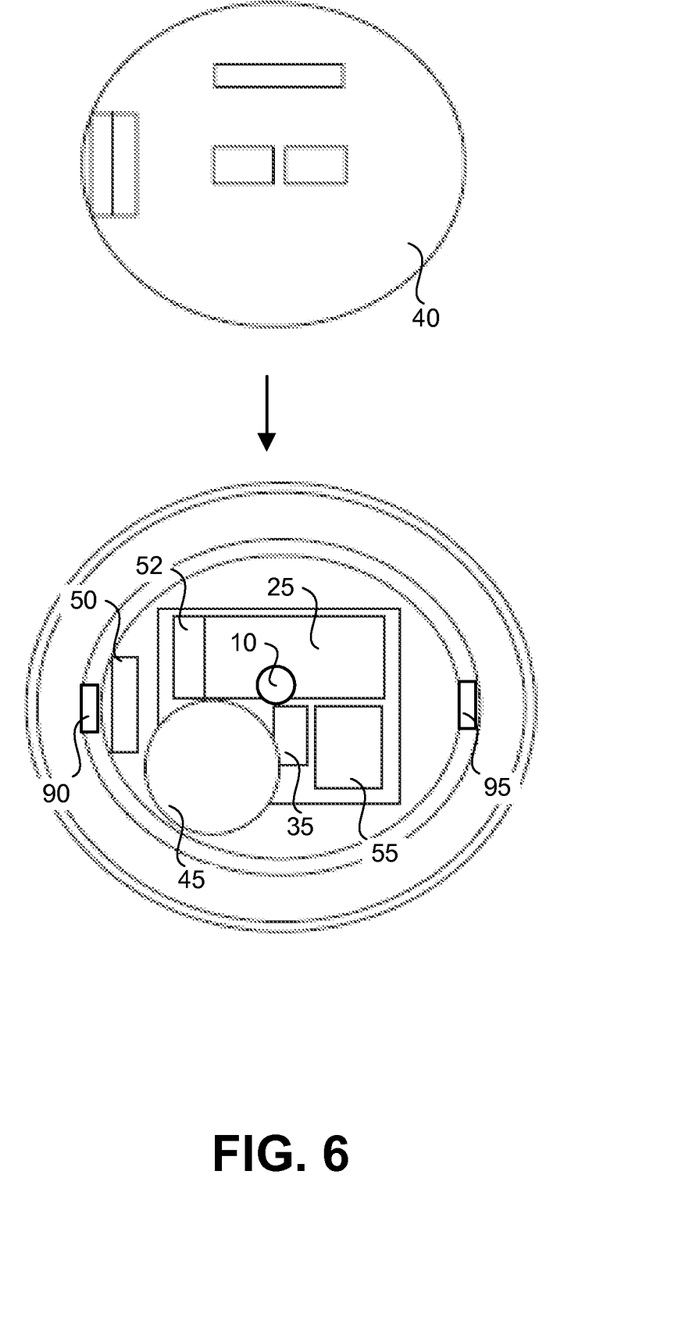
FIG. 6 is a top open view of the telemetry device with a top removed to illustrate some telemetry components in accordance with an embodiment of the present disclosure.

FIG. 6 is a top open view of the telemetry device with a top removed to illustrate some telemetry components in accordance with an embodiment of the present disclosure. Same or similar characteristics depicted in other figures may share the same reference numbers depicted herein. The telemetry device 5 comprises a female snap receptor 10, a detachable lid or top 40, a battery 45, multiple LED 50 to indicate battery energy or to indicate the Nth number of the respective telemetry device 5. The telemetry device also includes the wireless transmitter module 25 immediate and surrounding the female snap receptor 10, the programmable switch 35 and support electronics 55 and other supporting electronic components not depicted. A battery indicator is configured to flag a low battery energy level also in an embodiment of the present disclosure. The battery indicator may be one of a light emitting diode, an audible alarm and a vibration pulse device. The battery indicator enables battery replacement before the battery energy level drops below an energy level required for telemetry transmission. The indicators are perceptible to the patient and to medical staff and battery replacement may be performed by the patient or attending medical staff. An interface 90 and 95 on some discrete electrode telemetry devices may be configured to thread the plurality of devices in series to a single grounding device based on a connection and a disconnection of the single female snap receptor to the wireless transmitter module and the electrical ground thereof. One of the interface ports 90 and 95 may be a wireable connector port for a wired ground and another of the interface ports 90 and 95 may be a wireless connector port for a wireless ground according to predetermined technical, system and financial requirements.

In an embodiment of the disclosure, the wireless receiver module comprises a temporal multiplexor configured to assign a relative priority to a respective signal based on its initial arrival at the temporal multiplexor with respect to the arrival of other signals of the plurality of signals at the temporal multiplexor. The wireless receiver module is synchronized with the wireless transmitter module via a first to transmit protocol wherein the first wireless transmitter module to transmit is assigned a first synchronization and a second wireless transmitter module to transmit is assigned a second synchronization and so forth until a timeout period for a last wireless transmitter module to transmit has occurred.

Figure 7:
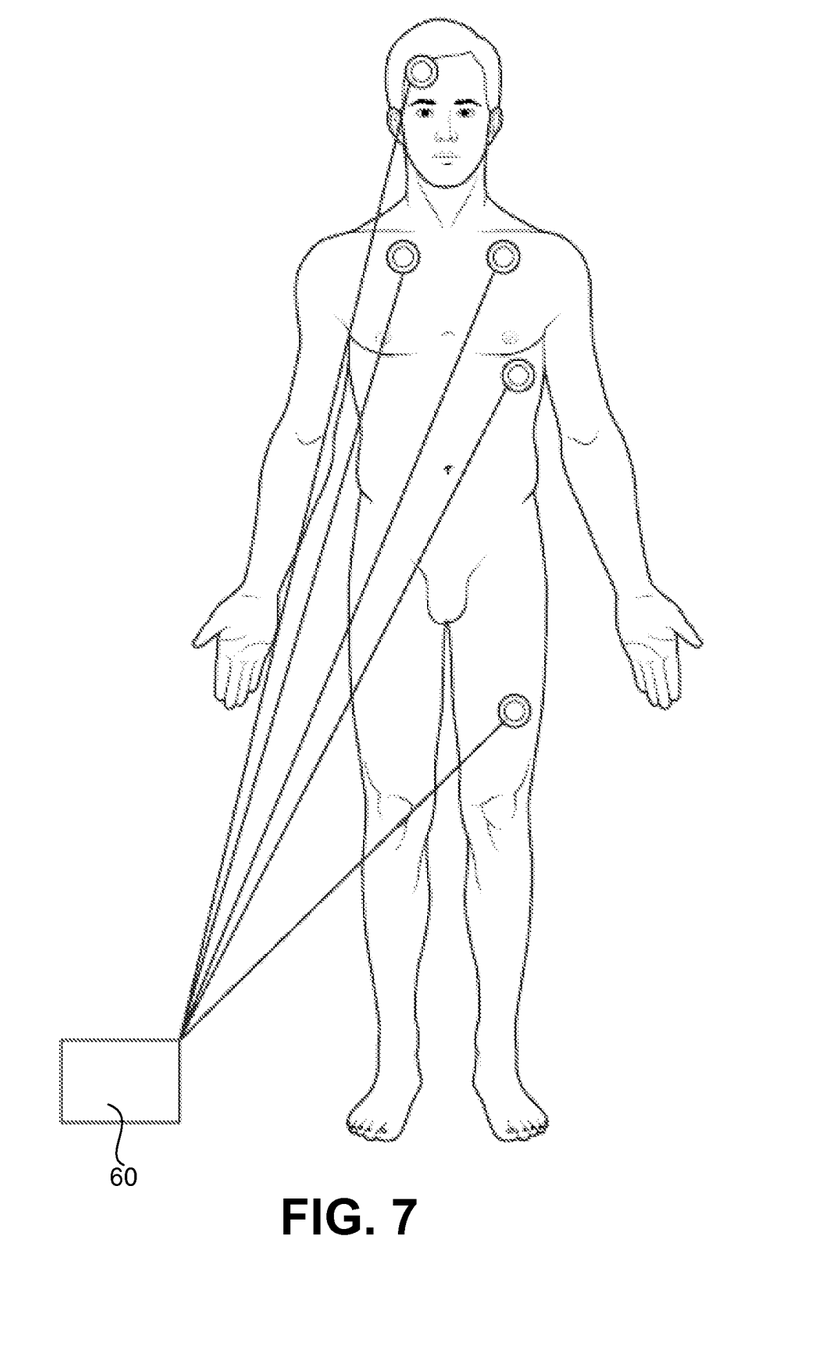
FIG. 7 is a pictorial view of the placement of several electrode patches and telemetry devices snapped thereto transmitting to a single remote receiver in accordance with an embodiment of the present disclosure.

FIG. 7 is a pictorial view of the placement of several electrode patches and telemetry devices snapped thereto transmitting to a single remote receiver in accordance with an embodiment of the present disclosure. Five electrode patches 20 and five telemetry devices 5 are snapped into pairs and placed on a patient as illustrated. A single receiver type 60 receives telemetry from the wireless transmitter module 25 of each telemetry device 5. The thigh placement of an electrode patch and telemetry device pair may be used as a ground or zero reference for processing the other Nth−1 signals which in this case is four.

In another embodiment of the disclosure, the wireless transmitter module comprises an encoder configured to encode a unique identifier into the signal, including but not limited to a direct current (DC) offset and a signal preamble. The encoded unique identifier is configured to be transmitted with the transmitted signal. The embodiment also includes a wireless receiver module comprises a decoder configured to decode each of the plurality of signals into separate respective signals for processing at the wireless receiver module. Also, an operational amplifier sensor is configured to sense a biological signal and amplify a signal difference into a voltage difference for transmission by the wireless transmitter.

Figure 8:
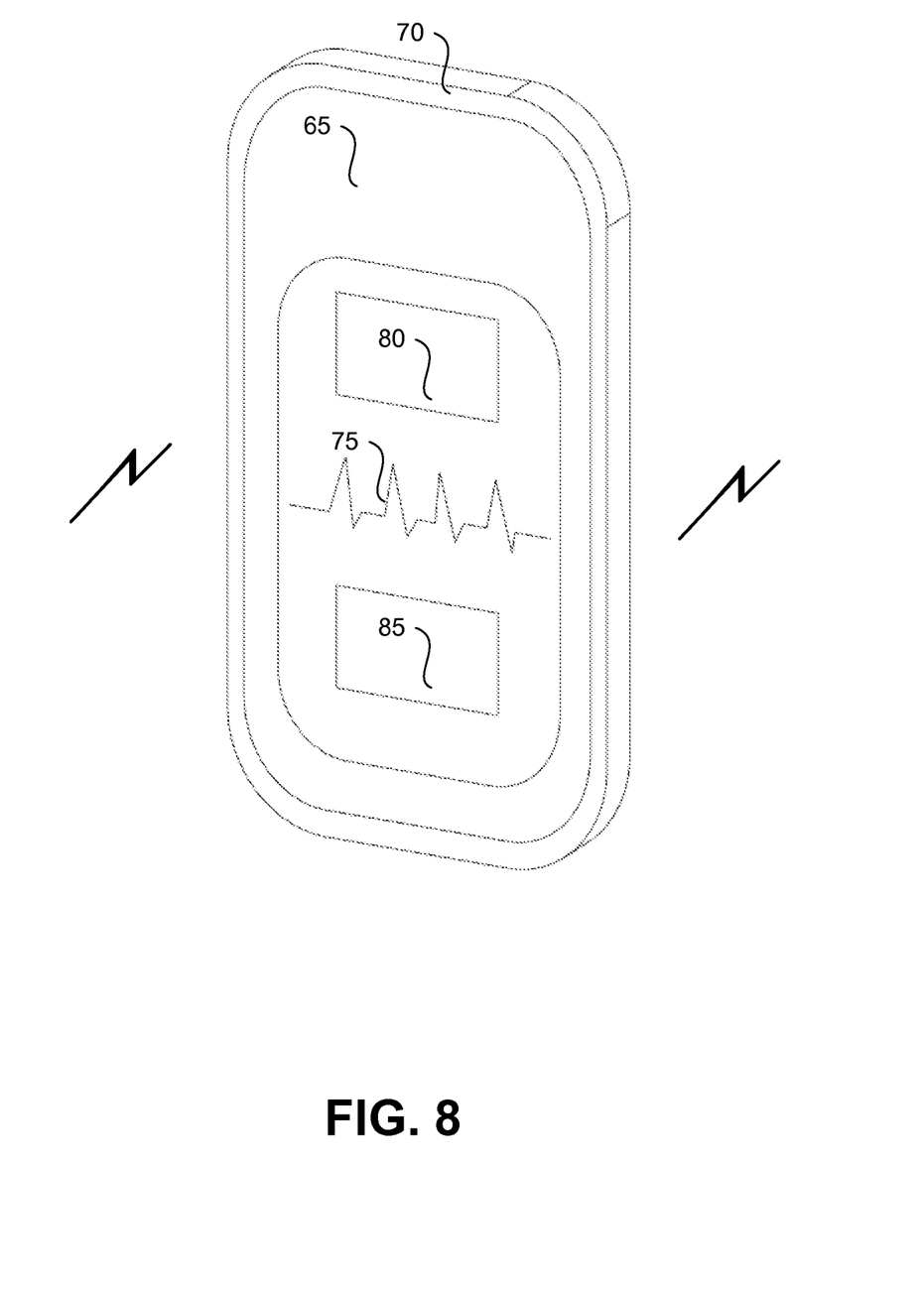
FIG. 8 is a pictorial view of a smart phone screen depicting processed transmissions in accordance with an embodiment of the present disclosure.

FIG. 8 is a pictorial view of a smart phone screen depicting processed transmissions in accordance with an embodiment of the present disclosure. The smart cell phone 65 is protected by a casing 70 which in some embodiments may receive telemetry signals and preprocess them before forwarding them to the cell phone for further processing. The waveform 75 is representative of a waveform received and processed at the cell phone but is not intended to be limiting to other waveforms receivable at the cell phone or any other receiver device. Screen areas 80 and 85 may be used to indicate information about the patient and information about the telemetry in progress such as the Nth number of signals in the telemetry and wireless and leadless electrode placement on the patient etc. The smart cell phone 65 may process radio frequencies and/or ultrasonic frequency transmissions according to applications programs and appended input and output devices. The casing 70 may interface with the smart phone 65 via electromagnetic waves or electromechanical connections. The applications programs may be configured to operate on either the smart phone 65 or the casing 70 or on both together and include a non-transitory computer readable medium having computer useable program code executable to perform operations of telemetry processing.

Figure 9:
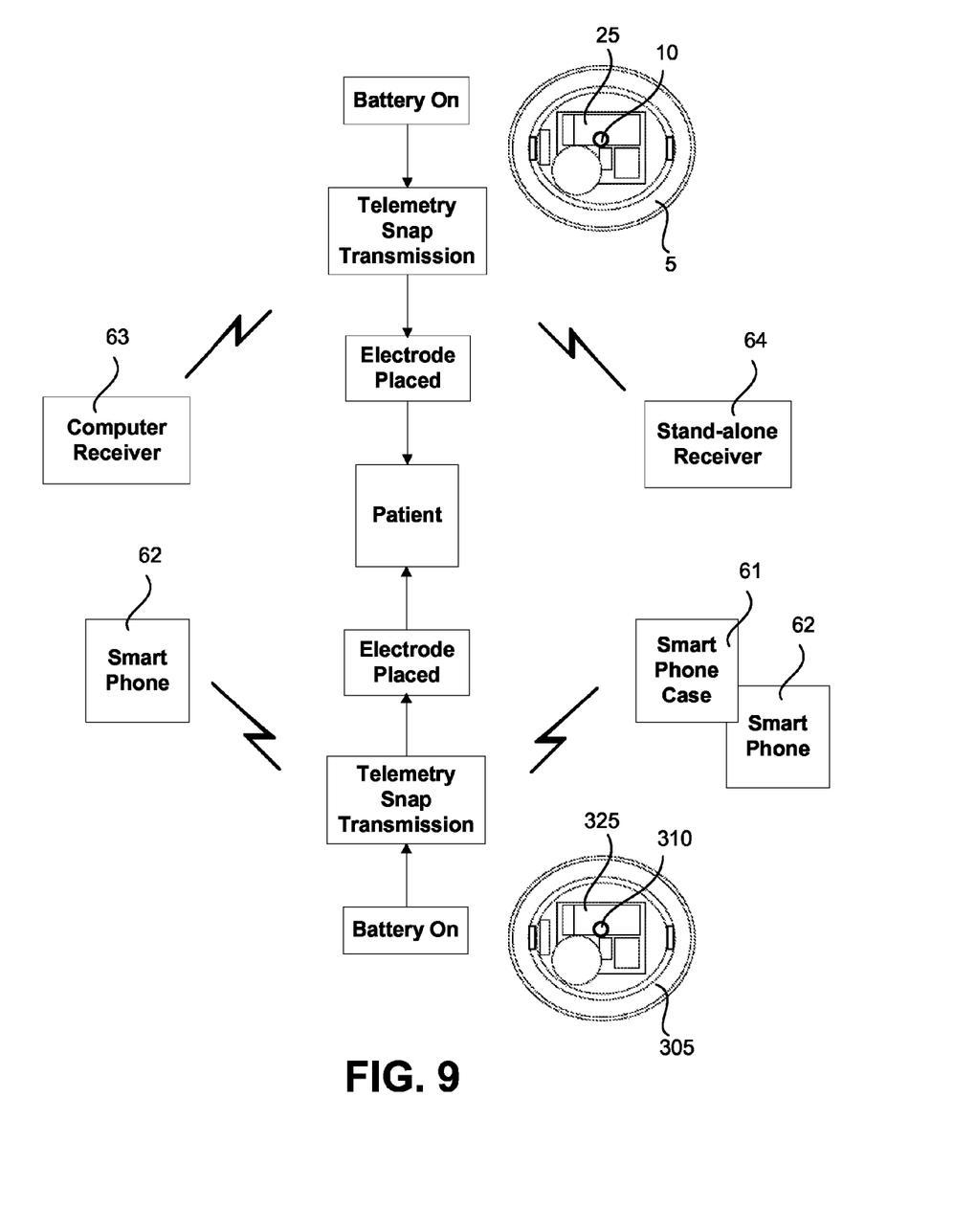
FIG. 9 is a block diagram of a telemetry system illustrating snap transmission of multiple placed electrodes and snapped telemetry devices on a patient in accordance with an embodiment of the present disclosure.

FIG. 9 is a block diagram of a telemetry system illustrating multiple snap transmission of multiple placed electrode and snapped telemetry devices on a patient in accordance with an embodiment of the present disclosure. Same reference numbers may indicate same or similar features of multiple telemetry devices. A telemetry system comprising an Nth number of telemetry devices 5 and an equal number of standard disposable electrode patches (not depicted). The system includes a female snap receptor 10 configured in a body of each of the telemetry devices 5. Each female snap receptor 10 is configured to attach to a single male snap post of an electrode patch. The system also includes a wireless transmitter module 25 disposed immediately around and in direct connection with each female snap receptor 10. Each respective wireless transmitter module 25 is configured to transmit a signal in reference to an electrical ground thereof from the respective female snap receptor 10 to a receiver module. The system further includes a wireless receiver module configured to receive and to process an Nth number of transmitted signals from the Nth number of telemetry devices into an Nth−1 number of signals where the number of signals is greater than zero. There are Nth−1 number of signals because at least one of the Nth telemetry devices is configured as a ground or zero volt reference for the rest of the Nth number of telemetry devices. The receiver module type may be a wireless phone case 61, a wireless phone 62, a computer 63 or any stand-alone device 64 able to process the five transmissions. The wireless phone case 61 is in electronic communication with the wireless phone 62. An Nth telemetry device 305 includes a female snap receptor 310 in a leadless body and a wireless transmitter module 325.

The telemetry system illustrated in FIG. 9 includes a 'battery on' indicator as a component of both telemetry devices 5, electrode patches 20 placed on a patient, two smart phones, a computer and a stand-alone receiver. Each telemetry device 5 is snapped onto an electrode patch 20 and the respective programmable switch 35 has activated a wireless transmission module to start a transmission, indicated 'Telemetry Snap Transmission.' The telemetry devices 5 are therefore in communication with a smart phone, the computer or the stand-alone device via radio waves and/or ultrasonic waves. The system therefore is in telemetry gathering mode for analyzing a patient's ECG or EKG or EEG activity. The first telemetry device to be snapped to an electrode patch and adhered to a patient may be designated the blue device and the second telemetry device to be snapped to an electrode patch and adhered to a patient may be designated the green device or the common ground or zero reference for the other telemetry device depending on where it is placed on the patient.

Figure 10:
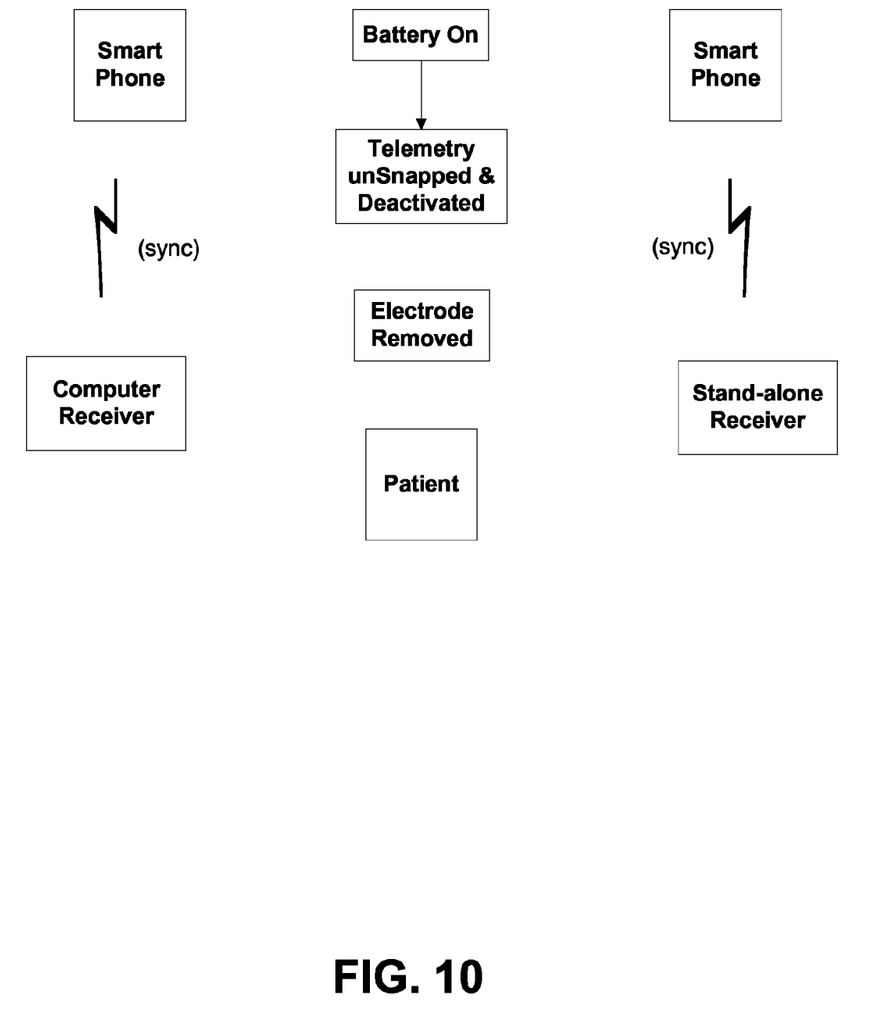
FIG. 10 is a block diagram of a telemetry system illustrating an unsnapped telemetry deactivation and a removed electrode patch in accordance with an embodiment of the present disclosure.

FIG. 10 is a block diagram of a telemetry system illustrating an unsnapped telemetry deactivation and a removed electrode patch in accordance with an embodiment of the present disclosure. The programmable switch 35 deactivates the wireless transmission module when the telemetry device 5 is unsnapped or removed from the electrode patch. This not only saves power but indicates to a receiver 60 that the telemetry device 5 has been removed from the patient and therefore may sound an alarm to attending medical staff or prevent erroneous telemetry. This is also an opportunity for synchronizing a cell phone to a computer or other stand-alone device.

Figure 11:
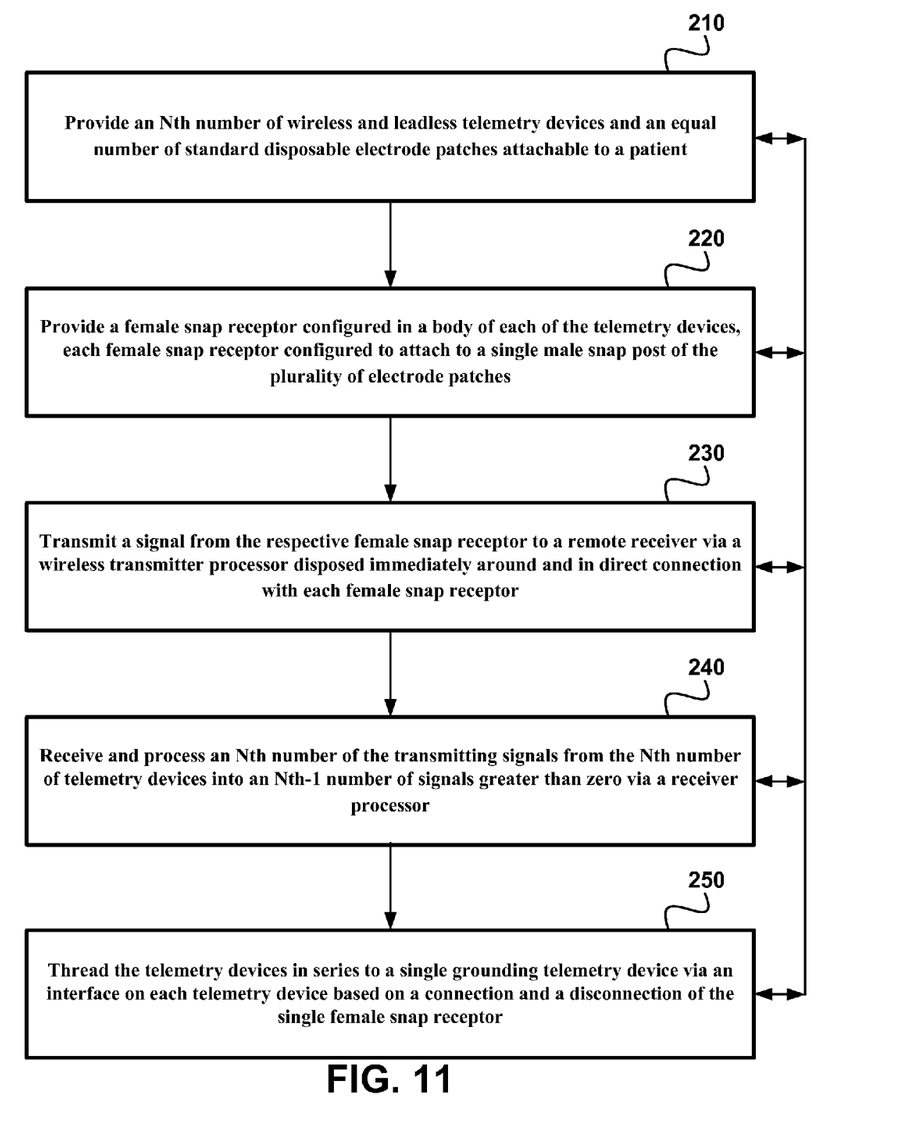
FIG. 11 is a block diagram of a method for telemetry including an Nth number of wireless and leadless telemetry devices and an equal number of standard disposable electrode patches attachable to a patient in accordance with an embodiment of the present disclosure.

FIG. 11 is a block diagram of a method for telemetry including an Nth number of wireless and leadless telemetry devices and an equal number of standard disposable electrode patches attachable to a patient in accordance with an embodiment of the present disclosure. A method for telemetry includes 210 providing an Nth number of wireless and leadless telemetry devices and an equal number of standard disposable electrode patches attachable to a patient is further disclosed. The method also includes 220 providing a female snap receptor configured in a body of each of the telemetry devices, each female snap receptor configured to attach to a single male snap post of the plurality of electrode patches. The method additionally includes 230 transmitting a signal from the respective female snap receptor to a remote receiver via a wireless transmitter processor disposed immediately around and in direct connection with each female snap receptor. The method further includes 240 receiving and processing an Nth number of the transmitting signals from the Nth number of telemetry devices into an Nth−1 number of signals greater than zero via a receiver processor. The method yet includes creating an Nth−1 number of composite signals including an Nth number of transmitting signals and a common ground reference signal. The method yet includes 250 threading the plurality of telemetry devices in series to a single grounding telemetry device via an interface on each telemetry device based on a connection and a disconnection of the single female snap receptor to the wireless transmitter module and the ground thereof.

An embodiment of the method of telemetry further comprises removing the wireless and leadless telemetry devices and leaving the electrode patches for one of patient hygiene, patient care and maintenance of the wireless and leadless telemetry devices including battery replacement. The embodiment may also comprise attaching the electrode patches onto a patient and snapping the wireless and leadless telemetry devices onto the electrode patches on the patient. The embodiment may further comprise snapping the wireless and leadless telemetry devices onto the electrode patches and creating a snapped pair for attaching onto a patient in a configuration including up to 18 electrode patches and an equal number of wireless and leadless telemetry devices and at least one wireless receiver processor A method of telemetry is disclosed in an embodiment of the disclosure comprising applying a specific color of an Nth plurality of various color light emitting diode (LED) telemetry devices to predetermined areas of a patient's body via the equal number of electrode patches, wherein an Nth color LED corresponds to a predetermined Nth area of a patient's body.

Figure 12A:
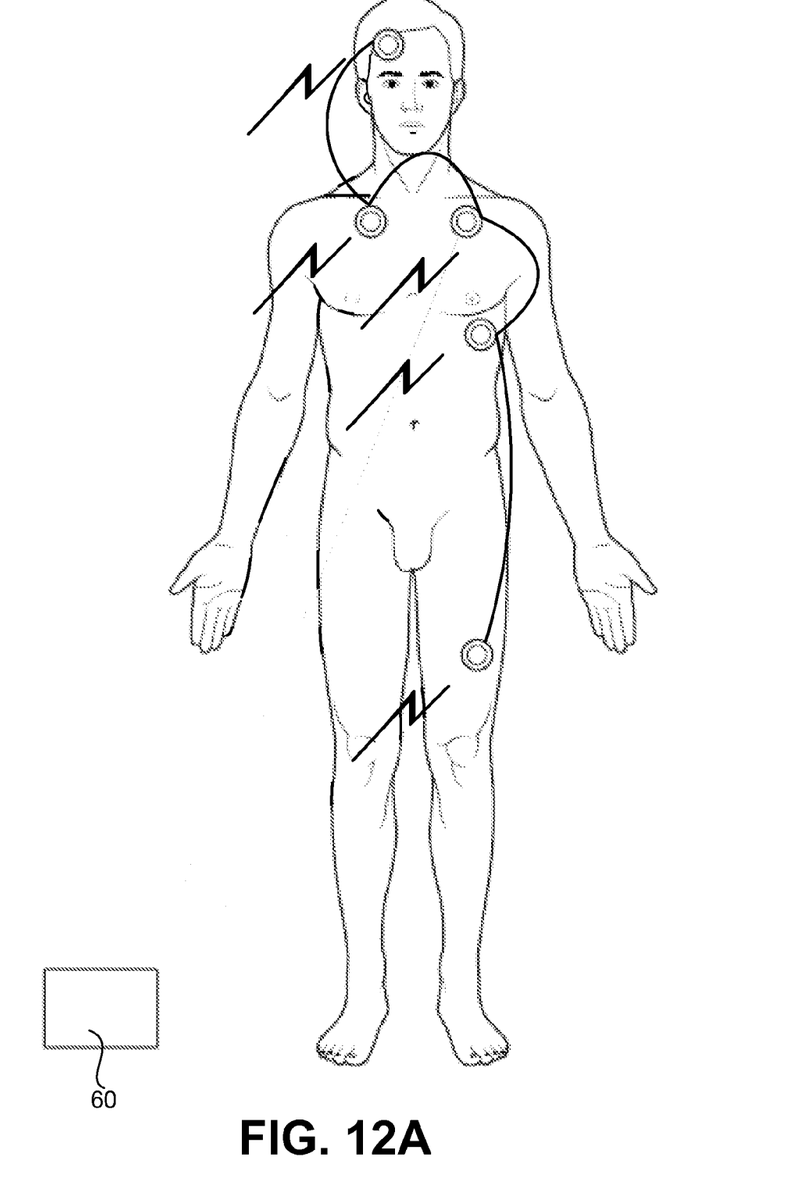
FIG. 12A is a pictorial view of the placement of several electrode patches and telemetry devices snapped thereto and an interface on each discrete electrode telemetry device configured to thread the devices in series to a single grounding telemetry device in accordance with an embodiment of the present disclosure.

FIG. 12A is a pictorial view of the placement of several electrode patches and telemetry devices snapped thereto and an interface on each discrete electrode telemetry device configured to thread the devices in series to a single grounding telemetry device in accordance with an embodiment of the present disclosure. There are five electrodes depicted in this pictorial but more than five may also be employed and placed according to the examination and telemetry information desired from the patient. The cranial electrode, the right chest electrode, the left chest electrode, the left rib electrode and the thigh electrode are all depicted in connection by a wired connector and interface configured to thread the devices in series to a single grounding telemetry device. The grounding telemetry device is conventionally located at the thigh but may also be located at any of the five electrode placements according to electrical ground information desired. The five telemetry devices and respective electrodes each communicate wirelessly with the remote receiver and receive an electrical ground from one of the five electrodes thus designated and determined by a snap connection to respective wireless transmitter module.

Figure 12B:
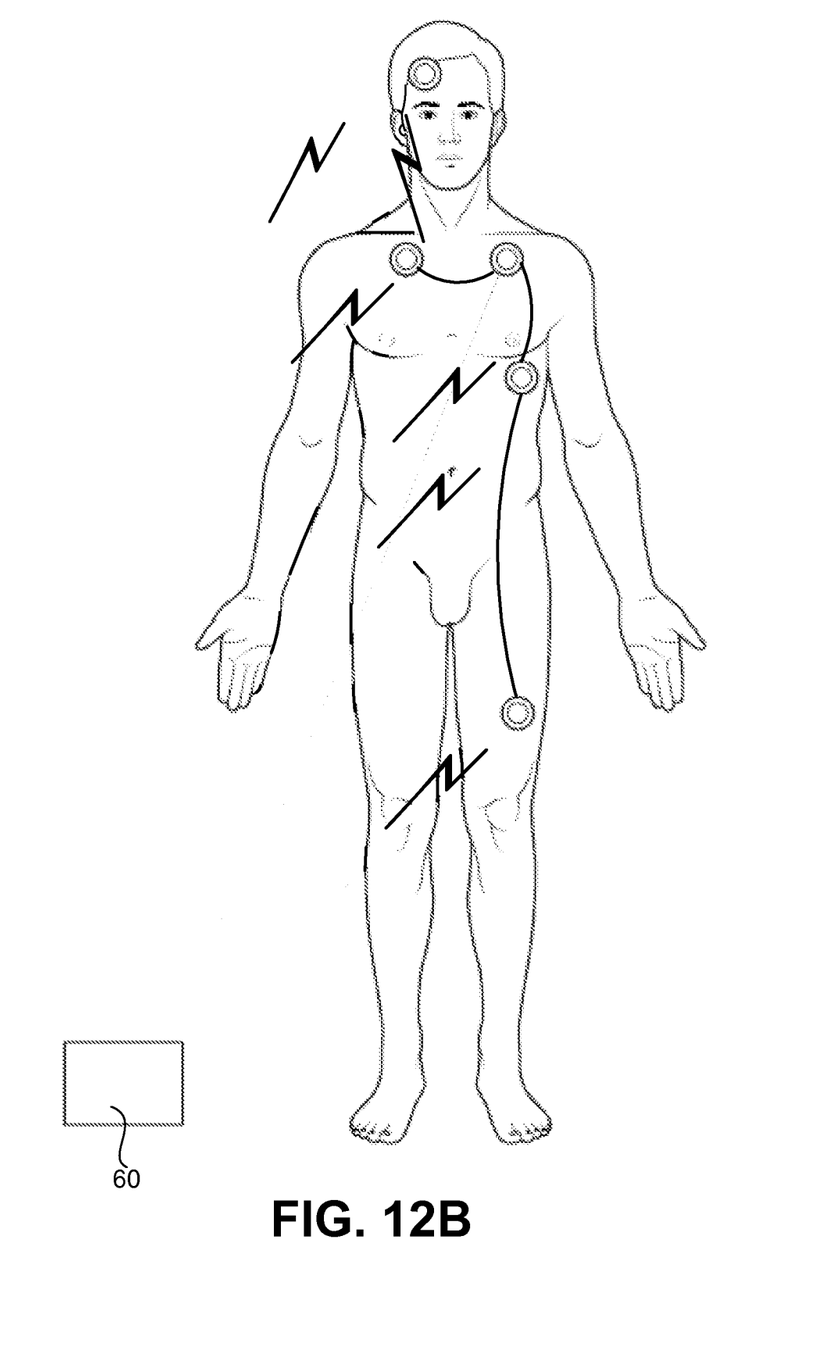
FIG. 12B is a pictorial view of the placement of several electrode patches and telemetry devices snapped thereto and a wired and wireless interface on each discrete electrode telemetry device configured to thread the devices in series to a single grounding telemetry device in accordance with an embodiment of the present disclosure.

FIG. 12B is a pictorial view of the placement of several electrode patches and telemetry devices snapped thereto and a wired and wireless interface on each discrete electrode telemetry device configured to thread the devices in series to a single grounding telemetry device in accordance with an embodiment of the present disclosure. There are five electrodes depicted in this pictorial but more than five may also be employed and placed according to the examination and telemetry information desired. The right chest electrode, the left chest electrode, the left rib electrode and the thigh electrode are all depicted in connection by a wired connector configured to thread the devices in series to a single grounding telemetry device. The grounding telemetry device is conventionally located at the thigh but may also be located at any of the five electrode placements according to the telemetry information desired. The cranial electrode is grounded wirelessly to the grounding electrode and therefore does not utilize a wired connector port interface but may utilize a wireless port to the grounding electrode. The grounding electrode may be any one of the discrete electrode telemetry devices. The thigh electrode may be grounding or the right or left chest electrode or the left rib electrode or any other electrode and does not need to be terminally connected in series but may be any electrode in the series chain, wired or wireless.

An embodiment of the disclosure may comprise the interface on each discrete electrode telemetry device configured to thread the plurality of devices in series to a single transmitting device based on a connection and a disconnection of the single female snap receptor to the respective wireless transmitter module and the respective signal to ground thereof. Therefore a signal may be transmitted in series through a physical wire or may be transmitted wirelessly in parallel with other signals from respective discrete electrode telemetry devices to the remote receiver.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

While the forgoing examples are illustrative of the principles of the present disclosure in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the disclosure be limited, except as by the specification and claims set forth herein.

What is claimed is:

1. A plurality of discrete electrode telemetry devices comprising:
   a) a single female snap receptor configured in a leadless body of a single discrete electrode telemetry device, the single female snap receptor configured to attach to a single male snap post of a single discrete standard circular disposable electrode patch;
   b) a wireless transmitter module disposed immediately around and in direct connection with the single female snap receptor, the wireless transmitter configured to transmit a signal in reference to an electrical ground thereof to a remote receiver; and
   c) an interface on each discrete electrode telemetry device configured to thread the plurality of devices in series to a single grounding device based on a connection and a disconnection of the single female snap receptor to the wireless transmitter module and the electrical ground thereof.

2. The plurality of discrete electrode telemetry devices of claim 1, wherein the plurality of discrete electrode telemetry devices comprises 3 or more devices and wherein the interface on each discrete electrode telemetry device comprises one of a wireless and a wired ground port in communication with the wireless transmitter and wherein the grounding device is any of the plurality of telemetry devices.

3. The plurality of discrete electrode telemetry devices of claim 1, further comprising a programmable switch configured to activate and deactivate a transmission of the wireless transmitter module based on a respective snap connection and a disconnection between the single female snap receptor and the single male snap post.

4. The plurality of discrete electrode telemetry devices of claim 1, further comprising a programmable switch including a non-transitory computer readable medium having computer useable program code executable to perform operations of an electronic switch configured to control the transmission of the wireless transmitter module despite a snap connection and a disconnection between the single female snap receptor and the single male snap post.

5. The plurality of discrete electrode telemetry devices of claim 1, wherein the wireless transmitter module is an ultrasound transmitter configured to transmit a signal in reference to an electrical ground thereof via ultrasound from the single female snap receptor to a remote receiver configured to receive an ultrasound transmission.

6. The plurality of discrete electrode telemetry devices of claim 1, wherein the wireless transmitter module is a radio frequency transmitter configured to transmit a signal in reference to an electrical ground thereof via radio frequencies from the single female snap receptor to a remote receiver configured to receive a radio frequency transmission.

7. The plurality of discrete electrode telemetry devices of claim 1, further comprising an Nth multicolor light emitting diode (LED) wherein an Nth color LED corresponds to a predeterminable Nth telemetry device number, the Nth telemetry device number configured to be transmitted with the transmitted signal.

8. The plurality of discrete electrode telemetry devices of claim 1, wherein the wireless transmitter module is configured to act as one of a master and a slave in one network and to alternatively act as a slave in another network in a multiple network master-slave protocol configured to enable communication by at least eight telemetry devices and at least one receiver.

9. The plurality of discrete electrode telemetry devices of claim 1, wherein the body of the single telemetry device is configured in a saucer-like chamfered perimeter shape having a radius similar to a radius of a US minted quarter and a total weight less than a weight of a US minted quarter.

10. A telemetry system comprising a plurality of discrete electrode telemetry devices, comprising:
    a) an Nth plurality of button-like wireless and leadless discrete electrode telemetry devices and an equal plurality of standard circular disposable electrode patches;
    b) a single female snap receptor configured in a leadless body of each of the discrete electrode telemetry devices, each female snap receptor configured to attach to a single male snap post of the plurality of standard circular disposable electrode patches;
    c) a wireless transmitter module disposed immediately around and in direct connection with each female snap receptor, each respective wireless transmitter module configured to transmit a signal in reference to an electrical ground thereof to a receiver;
    d) a wireless receiver module configured to receive and to process an Nth plurality of transmitted signals from the Nth plurality of discrete electrode telemetry devices into an Nth−1 number of signals greater than zero; and
    e) an interface on each discrete electrode telemetry device configured to thread the plurality of telemetry devices in series to a single grounding telemetry device based on a connection and a disconnection of the female snap receptor to the wireless transmitter module and the ground thereof.

11. The telemetry system of claim 10, wherein at least one of the Nth plurality of discrete electrode telemetry devices is configured as a ground reference device for the rest of the Nth plurality of telemetry devices.

12. The telemetry system of claim 10, further comprising an Nth plurality of various color light emitting diodes (LED) wherein an Nth color LED corresponds to a Nth telemetry device number, the Nth telemetry device number configured to be transmitted with the transmitted signal.

13. The telemetry system of claim 10, wherein the wireless transmitter module is configured to act as one of a master and a slave in one network and to alternatively act as a slave in another network in a multiple network master-slave protocol to enable communication by more than 8 telemetry devices and at least one remote receiver.

14. The telemetry system of claim 10, wherein the wireless receiver module is synchronized with the wireless transmitter module via a temporal multiplexor wherein the first wireless transmitter module to transmit is assigned a first synchronization and a second wireless transmitter module to transmit is assigned a second synchronization and so forth until a timeout period for a last wireless transmitter module to transmit has occurred.

15. The telemetry system of claim 10, wherein the receiver module resides in a cell phone casing configured to communicate a composite transmission to the cell phone for processing and a stand-alone unit capable of communicating with a personal computer.

16. A method for telemetry, the method comprising:
    a) providing an Nth plurality of wireless and leadless discrete electrode telemetry devices and an equal plurality of standard circular disposable electrode patches attachable to a patient;

b) providing a single female snap receptor configured in a leadless body of each of the discrete electrode telemetry devices, each female snap receptor configured to attach to a single male snap post of the plurality of standard circular disposable electrode patches;

c) transmitting a signal in reference from the respective female snap receptor to a remote receiver via a wireless transmitter processor disposed immediately around and in direct connection with each female snap receptor;

d) receiving and processing an Nth plurality of the transmitting signals from the Nth plurality of discrete electrode telemetry devices into an Nth−1 number of signals greater than zero via a receiver processor; and e) threading the plurality of telemetry devices in series to a single grounding telemetry device via an interface on each telemetry device based on a connection and a disconnection of the single female snap receptor to the wireless transmitter module and the ground thereof.

17. The method of telemetry of claim 16, further comprising creating an Nth−1 number of composite signals including an Nth transmitting signal and a common ground reference signal.

18. The method of telemetry of claim 16, further comprising removing the wireless and leadless telemetry devices and leaving the electrode patches for one of patient hygiene, patient care and maintenance of the wireless and leadless telemetry devices including battery replacement.

19. The method of telemetry of claim 16, wherein the plurality of discrete electrode devices comprises at least 3 devices and wherein an interface on each discrete electrode telemetry device comprises one of a wireless and a wired ground port in communication with the wireless transmitter.

20. The method of telemetry of claim 16, further comprising snapping the wireless and leadless telemetry devices onto the electrode patches and creating a snapped pair for attaching onto a patient in a configuration including up to 18 electrode patches and an equal number of wireless and leadless telemetry devices and at least one wireless receiver processor.

* * * * *